United States Patent [19]

Drury et al.

[11] Patent Number: 4,853,482

[45] Date of Patent: Aug. 1, 1989

[54] PROCESS FOR THE PREPARATION OF ACIDS

[75] Inventors: David J. Drury, Twickenham; John E. Hamlin, Hull, both of England

[73] Assignee: BP Chemicals Limited, London, England

[21] Appl. No.: 545,150

[22] Filed: Oct. 25, 1983

[30] Foreign Application Priority Data

Nov. 4, 1982 [GB] United Kingdom ............... 8231526

[51] Int. Cl.$^4$ ...................... C07C 51/12; C07C 53/08; C07C 53/126
[52] U.S. Cl. .................................. 562/607; 260/413; 562/606
[58] Field of Search ...................... 562/606, 607, 517; 260/413

[56] References Cited

U.S. PATENT DOCUMENTS 3,839,428 10/1974 Isogai .................................. 562/607

FOREIGN PATENT DOCUMENTS 1286224 8/1972 United Kingdom ............... 562/606

Primary Examiner—Vivian Garner
Attorney, Agent, or Firm—Brooks Haidt Haffner & Delahunty

[57] ABSTRACT

A carboxylic acid of formula $RCO_2H$ where R is a $C_1$ to $C_{10}$ aliphatic hydrocarbyl group is prepared by heating under substantially anhydrous conditions an ester of formic acid of formula $HCO_2R$ where R is as defined above in the presence of carbon monoxide and an effective amount of a catalyst system comprising a Group VIII metal, a halide and a compound containing a quaternary Group V atom. The quaternary Group V atom can be formed in situ by adding a compound containing a trivalent nitrogen, phosphorus or arsenic atom quaternizable under the reaction conditions and a quaternizing agent. Acetic acid is prepared by heating methyl formate in the presence of a catalyst system containing a rhodium compound, an iodide and a quaternary nitrogen-containing heterocyclic base.

3 Claims, No Drawings

PROCESS FOR THE PREPARATION OF ACIDS

This invention relates to a process for the preparation of carboxylic acids more particularly to the preparation of aliphatic carboxylic acids by the isomerisation of esters of formic acid.

The conversion of esters of formic acid to the corresponding carboxylic acid in the presence of carbon monoxide and a Group VIII metal catalyst has been previously described in U.S. Pat. No. 3,839,428.

Further GB Pat. No. 1,286,224 discloses a process for the preparation of acetic acid by heating methyl formate in the presence of carbon monoxide, a rhodium catalyst and a halogen promoter.

It has now been found that the conversion of the formate ester can be greatly increased as compared with these previously described processes by including in the catalyst system a compound containing a quaternary Group V atom.

Thus, according to the present invention a process for the preparation of a carboxylic acid of formula $RCO_2H$ where R is a $C_1$ to $C_{10}$ aliphatic hydrocarbyl group comprises heating under substantially anhydrous conditions an ester of formic acid of formula $HCO_2R$ where R is as defined above in the presence of carbon monoxide and an effective amount of a catalyst system comprising a Group VIII metal, a halide and a compound containing a quaternary Group V atom.

The R group can conveniently be a saturated or unsaturated aliphatic group and can be a $C_1$ to $C_6$ alkyl group, a $C_2$ to $C_6$ alkenyl or alkynyl or a $C_4$ to $C_{10}$ alicyclic group.

Conveniently the Group VIII metal is a noble metal. By Group VIII noble metal is meant ruthenium, rhodium, palladium, osmium, iridium and platinum. Rhodium is preferred. The metal component may suitably be the elemental metal of a compound containing the metal, such as an oxide, a salt, an organometallic compound or a coordination compound.

The halide can be added as the free halogen, as the hydrogen halide, as RX where X is the halide and R is as defined above or as the preformed quaternised Group V atom salt.

Conveniently the concentration of catalyst is at least 100 ppm (parts by weight of the metal based on the weight of the reaction mixture), for example in the range 100 to 2500 ppm, preferably 500 to 2000 ppm.

Conveniently the ratio of moles of Group V compared to gm atoms of Group VIII metal is from 1:2 to 100:1, preferably at least 1:1.

Conveniently the atomic ratio of Group VIII metal to halide is from 1:20 to 1:1000, preferably 1:40 to 1:800

The quaternary Group V atom can be nitrogen, phosphorus or arsenic. Nitrogen is preferred. The quaternary Group V atom can be formed by adding a compound containing a trivalent nitrogen, phosphorus or arsenic atom quaternisable under the reaction conditions and a quaternizing agent.

Conveniently the compound containing trivalent nitrogen or phosphorus or arsenic is of the formula

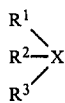

where X is nitrogen, phosphorus or arsenic and the $R^1$, $R^2$ and $R^3$ are $C_1$ to $C_{10}$ groups, where two or more can optionally form part of a cyclic structure.

The quaternizing agent can be an alkyl iodide or bromide, for example, a $C_1$ to $C_6$ alkyl iodide. Suitable relative molar amounts of quaternizing agent to trivalent Group V compound are from 5:1 to 1:5, but preferably from 3:1 to 1:3.

The amount of carbon monoxide should preferably be such as to provide a pressure of 10 to 300 bar, preferably 20 to 150 bar.

Other gases such as hydrogen or an inert gas may be present, in which case the partial pressure or carbon monoxide may be within the ranges specified above.

Conveniently the reaction is effected at a temperature in the range 75° to 300° C. preferably 150° to 250° C.

Preferably the reactants and products (with the exception of the carbon monoxide) are maintained in the liquid phase and the catalyst system is employed in solution in a solvent compatible with the catalyst.

A preferred solvent is a monocarboxylic acid having 2 to 11 carbon atoms, e.g. acetic, propionic, hexanoic or decanoic acid. Preferably the solvent is the same carboxylic acid as that produced in the reaction for example in the isomerisation of methyl formate the preferred solvent is acetic acid.

The reaction can however be effected in the gas phase or liquid phase with the catalyst system supported on an inert solid support.

The reaction can be effected batchwise or continuously.

The term substantially anhydrous conditions is not intended to exclude water in minor amounts as would be supplied by ordinary commercial forms of the reactants.

The invention is illustrated by the following examples in which the reactants employed were ordinary commercially available materials and the reactants and products (except the carbon monoxide) were maintained in the liquid phase and the catalyst system was employed in solution. Propionic acid was used as solvent to aid analysis for acetic acid as product.

Comparative Experiment 1

Not according to the invention and included for comparative purposes only.

Into an autoclave of 500 ml capacity made of corrosion resistant metal and fitted with a rotary stirrer were charged 121.8 g methyl formate, 39.1 g methyl iodide, 0.8 g rhodium diacetate and 103.2 g propionate acid. The autoclave was closed and carbon monoxide was introduced to 25 atms pressure and then heated to 185° C. The autoclave was maintained at this temperature for 30 minutes, cooled to room temperature and the pressure released. The liquid product was removed from the autoclave and a small portion analysed by gas liquid chromatography. This indicated that the conversion to acetic acid was 12.0% at a rate of 2 moles acetic acid per liter of reaction solution per hour.

EXAMPLE 1

Into the same reactor system as Experiment 1 were charged 121.8 g methyl formate, 63.2 g methyl iodide, 13.8 g N-methyl imidazole, 0.8 g rhodium diacetate and 103.0 g propionic acid. The autoclave was closed and carbon monoxide was introduced to 24 atms pressure and then heated to 185° C. The autoclave was maintained at this temperature for 30 minutes, cooled to room temperature and the pressure released. The liquid product was removed from the autoclave and a small portion analysed by gas liquid chromatography. This indicated that the conversion to acetic acid was 91.2% at a rate of 11.2 moles acetic acid per liter of reaction solution per hour.

This example shows that, as compared with experiment 1, the presence of the quaternisable nitrogen-containing base in the form of N-methyl imidazole gives a much higher catalyst activity under similar conditions.

EXAMPLE 2

Into the same reactor system as Example 1 were charged 122.0 g methyl formate, 24.0 g methyl iodide, 13.8 g N-methyl imidazole, 0.8 g rhodium diacetate and 103.0 g propionic acid. The autoclave was closed and carbon monoxide was introduced to 24 atms pressure and then heated to 185° C. The autoclave was maintained at this temperature for 30 minutes, cooled to room temperature and the pressure released. The liquid product was removed from the autoclave and a small portion analysed by gas-liquid chromatography. This indicated that the conversion to acetic acid was 27.7% at a rate of 4.3 moles acetic acid per liter of reaction solution per hour.

EXAMPLE 3

Into the same reactor system as Example 1 were charged 121.8 g methyl formate, 37.7 g of N,N-dimethyl imidazolium iodide, 0.8 g rhodium diacetate and a 103.0 g of propionic acid. The autoclave was closed and carbon monoxide was introduced to 24 atms pressure and then heated to 185° C. The autoclave was maintained at this temperature for 30 minutes, cooled to room temperature and the pressure released. The liquid product was removed from the autoclave and a small portion anlaysed by gas-liquid chromatography. This indicated that this conversion to acetic acid was 13.1% at a rate of 3.6 moles acetic acid per liter of reaction solution per hour.

Examples 2 and 3 show that the quaternary ammonium salt as promoter may be formed in situ (Example 2) or may be preformed (Example 3).

Table showing ratios of the components and catalyst concentrations in the examples.

|  | Experiment 1 | Example 1 | Example 2 | Example 3 |
|---|---|---|---|---|
| Ratio. moles GpV compound:gm atoms of rhodium | — | 49.4 | 46.2 | 46.5 |
| Iodide:rhodium atomic ratio | 75.8 | 122.3 | 46.5 | 46.5 |
| Molar ratio Iodide:Gpv compound | — | 2.6 | 1.0 | 1.0 |
| Rhodium concentration parts per million | 1390 | 1210 | 1390 | 1390 |

We claim:
1. A process for the preparation of a carboxylic acid of formula $RCO_2H$ where R is a $C_1$ to $C_{10}$ aliphatic hydrocarbyl group which process comprises heating under substantially anhydrous conditions an ester of formic acid of formula $HCO_2R$ where R is as defined above in the presence of carbon monoxide and an effective amount of a catalyst system comprising a Group VIII metal, a halide and a compound containing a quaternary Group V atom, wherein the quaternary Group V atom is formed by adding a compound containing a trivalent nitrogen atom quaternizable under the reaction conditions and a quaternizing agent and wherein said compound containing a trivalent quaternizable nitrogen atom is N-methyl imidazole.

2. A process for the preparation of acetic acid which process comprises heating under substantially anhydrous conditions methyl formate in the presence of carbon monoxide and an effective amount of a catalyst system comprising a rhodium compound, an iodide and a quaternized imidazole.

3. A process as claimed in claim 2, wherein said quaternised imidazole is N,N-dimethyl imidazolium iodide.

* * * * *

UNITED STATES PATENT AND TRADEMARK OFFICE
CERTIFICATE OF CORRECTION

PATENT NO.   : 4,853,482
DATED        : August 1, 1989
INVENTOR(S)  : DAVID J. DRURY et al It is certified that error appears in the above-identified patent and that said Letters Patent is hereby corrected as shown below:

Col. 2, l. 50, should read, "..and 103.2 g _propionic_ acid.."

Signed and Sealed this

Tenth Day of July, 1990

*Attest:*

HARRY F. MANBECK, JR.

*Attesting Officer*  *Commissioner of Patents and Trademarks*